United States Patent [19]

Jones

[11] Patent Number: 4,962,760
[45] Date of Patent: Oct. 16, 1990

[54] ORTHOPEDIC RESTRAINT APPARATUS

[75] Inventor: Robert W. Jones, San Antonio, Tex.
[73] Assignee: Mesa, Inc., San Antonio, Tex.
[21] Appl. No.: 345,563
[22] Filed: May 1, 1989
[51] Int. Cl.⁵ ............................................... A61F 5/00
[52] U.S. Cl. .................................... 128/80 F; 128/88; 36/31; 36/104
[58] Field of Search ................ 128/80 F, 80 G, 80 H, 128/88; 36/33, 31, 104

[56] References Cited

U.S. PATENT DOCUMENTS

| | | | |
|---|---|---|---|
| 2,517,472 | 8/1950 | Fathauer | 36/33 X |
| 2,522,515 | 9/1950 | Hill | 36/33 X |
| 2,558,986 | 7/1951 | Seelert | 128/80 F |
| 3,827,431 | 8/1974 | Pecorella | 128/80 F |
| 4,614,181 | 9/1986 | Karlsson | 128/80 F X |
| 4,771,768 | 9/1988 | Crispin | 128/80 H X |

Primary Examiner—Edgar S. Burr
Assistant Examiner—Moshe I. Cohen
Attorney, Agent, or Firm—Thomas E. Sisson

[57] ABSTRACT

An orthopedic restraint apparatus having lower leg brace members, a contoured foot support, an adjustable ankle joint articulation system, and a hingedly mounted toe member. The ankle joint articulation system is easily adjustable to a multiplicity of discrete flexion angles by the appropriate placement of limit pins in the ankle joint. The limit pins are removable in a direction perpendicular to the longitudinal axis of the leg brace members.

1 Claim, 2 Drawing Sheets

ORTHOPEDIC RESTRAINT APPARATUS

BACKGROUND OF THE INVENTION

This invention relates to an improved orthopedic restraint apparatus, more particularly to an orthopedic foot support and restraint with controlled ankle flexion having a hinged forefoot member and a reduced height heel portion.

Existing orthopedic walking casts or braces generally have a highly elevated heel portion, an arcuated midfoot portion, and a rigid forefoot portion. The arcuated midfoot allows for the wearer's foot, during walking, to rotate along the arcuation and is intended to result in a smoother gait. Unfortunately, the arcuation results in a significantly higher vertical displacement of the foot above the walking surface, which in turn results in a very uneven and awkward hip joint rotation.

SUMMARY OF THE INVENTION

The present invention utilizes a heel, midfoot, and forefoot which essentially raises the foot approximately the same distance above the walking surface as does a standard shoe heel and sole. No arcuated midfoot is required with the present invention as the result of the incorporation of a forefoot member having a hinge located at the point approximately where the toes meet the foot. Further, a simplified ankle articulation control system is provided to allow incremental plantarflexion and dorsiflexion over a total range of 60°.

DETAILED DESCRIPTION OF THE PREFERRED EMBODIMENT

Figure 1:
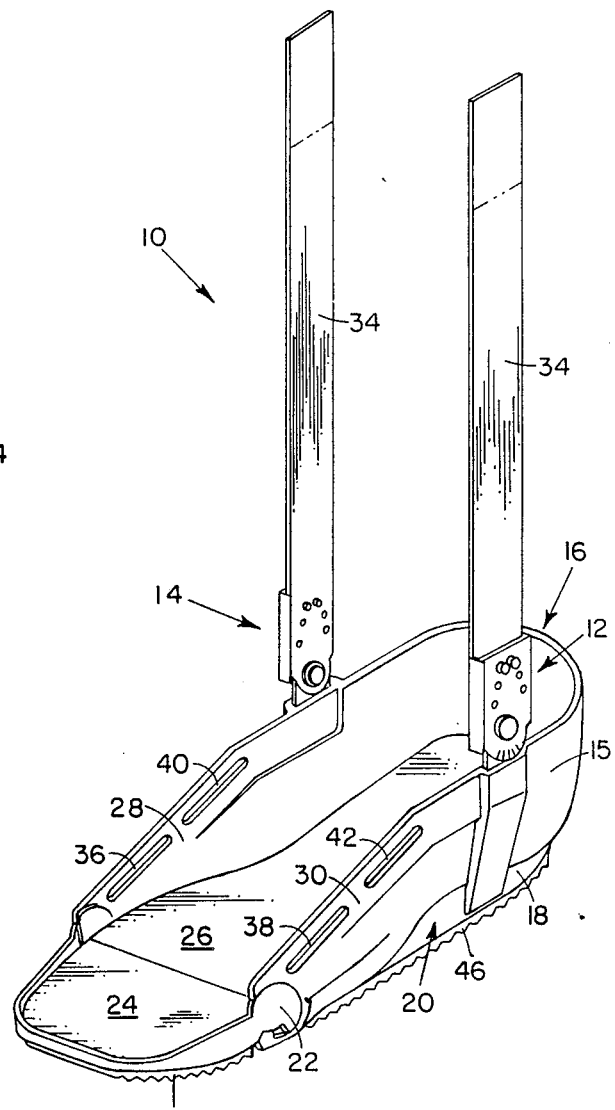
FIG. 1 is a left, front perspective view of the present invention.

FIG. 1 illustrates the present invention 10 with ankle joints 12 and 14, contoured foot support 15, heel cup 16, heel base 18, midfoot portion 20, toe hinge 22, toe member 24, foot pad 26, side walls 28 and 30, and upper brace members 32 and 34. FIG. 1 shows the invention 10 with ankle joints 12 and 14 in the zero flexion position and toe member 24 also in the zero flexion position. Lower strap slots 36 and 38 and upper strap slots 40 and 42 are formed in the side walls 28 and 30 to accommodate restraint straps, not shown, when the invention is affixed to a patient's foot. The upper brace members are also securely attached around the lower portion of the patient's leg by any number of methods such as straps or tape. Invention 10 is also provided with a toe traction tread 44 attached to the bottom of toe member 24 and a midfoot/heel traction tread 46 securely affixed to the bottom of midfoot portion 20 and heel base 18.

Figure 2A:
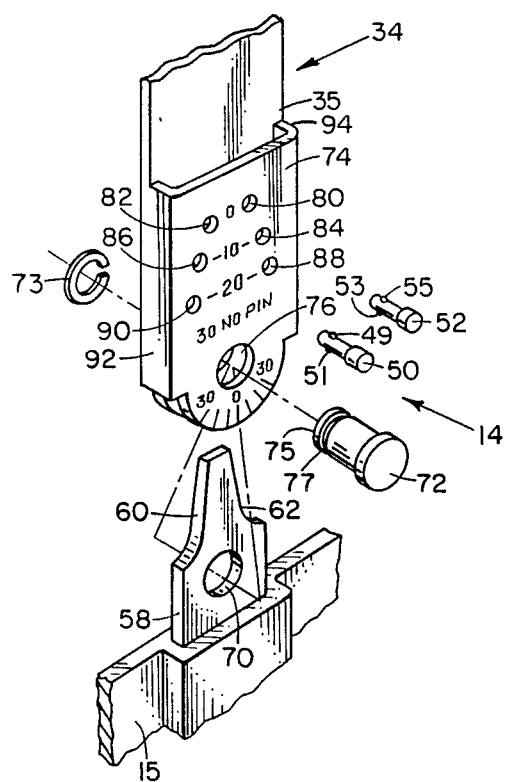
FIG. 2A is an enlarged exploded perspective view of the ankle articulation control system of the present invention.
Figure 2B:
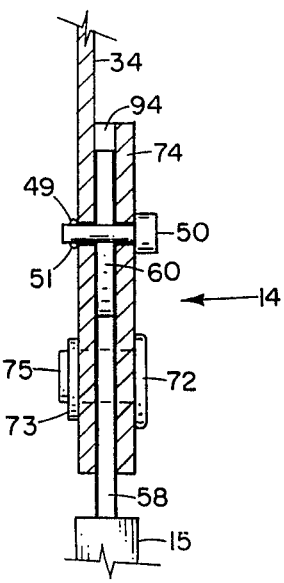
FIG. 2B is a sectional view of the ankle articulation control system of the present invention.
Figure 2:
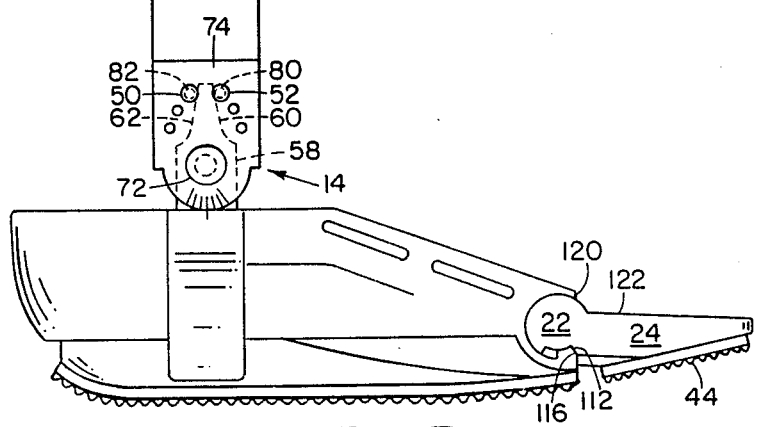
FIG. 2 is a right side elevation view of the present invention in the zero flexion position.

Turning to FIG. 2, ankle joint 14 is shown in the zero flexion position with ankle flexion limit pins 50 and 52 in uppermost flexion adjustment holes 80 and 82 respectively. Shown in dotted lines is ankle riser member 58 with arcuated edges 60 and 62. The top end 64 of riser 58 is dispositioned between pins 50 and 52 thereby restricting the articulation of upper brace member 34 in either the dorsal (toward the back or heel) or plantar (toward the front or sole) directions.

A riser 58 is rigidly secured in the vertical position extending upwardly from each of the side walls of foot support 15.

FIG. 2A is an enlarged, exploded perspective view of the ankle articulation control system of the present invention for ankle joint 14. Riser 58 may be seen extending vertically from foot support 15. Pivot pin orifice 70 is formed in riser 58 to accommodate pivot pin 72. At the lower end 35 of brace member 34 is formed a riser channel 74 into which may be slid riser 58 when ankle joint 14 is assembled. When fitted together with riser 58 inserted into channel 74, pivot pin orifice 76 in channel 74 is aligned with orifice 70 in riser 58, and pivot pin 72 is passed through orifices 76 and 70 to pivotally connect the foot support 15 to brace member 34. Retainer 73 is snapped over end 75 of pin 72 and secured in groove 77. In a similar fashion, brace member 32 is attached to the opposite riser on the opposite side of foot support 15.

The angle of flexion in joint 14 is controlled by the placement of limit pins 50 and 52 in the flexion adjustment holes 80, 82, 84, 86, 88, and 90. It should be understood that flexion and control of joint 16 is controlled in a like manner. When no limit pins are used, brace member 34 is capable of 30° plantar and dorsiflexion because riser 58 will abut against front wall 94 or rear wall 92 of channel 74 as brace 34 is pivoted in the dorsal direction or plantar direction, respectively.

Adjustment holes 84 and 86 are dispositioned in channel 74 so as to allow movement of brace 34 10° either in the dorsal or plantar directions when pins 50 and 52 are inserted in holes 84 and 86. Pins 50 and 52 abut against arcuated edges 60 and 62 of riser 58 thereby limiting pivotal movement of brace 34. A 20° flexion in either direction may be achieved by placing pins 50 and 52 in adjustment holes 88 and 90. Further, it should be understood from the above description and the figures that combinations of flexion angles may result by various placement of pins 50 and 52 in the adjustment holes. For example, by placing pin 50 in hole 82 and pin 52 in hole 78, brace 34 is adjustable to 0° dorsiflexion and 20° plantarflexion.

Pins 50 and 52 are easily removable from the adjustment holes from the outside or exposed side of brace 34 without the use of a separate tool or implement such as a wrench or screwdriver. The pins are removed in a generally perpendicular direction relative the longitudinal axis of brace member 34. Pins 50 and 52 are secured in place by spring-loaded balls 49, 51, 53, and 55 which are urged outwardly by internal springs in pin 50 and 52. Thus, a doctor, therapist, or even the patient, may readjust the flexion of the brace by pulling a limit pin out of an adjustment hole and reinserting it at a new location. No special tools or implements are required. This easy accessibility for adjustment is not known in this particular art.

A sectional view of ankle joint 14 is illustrated in FIG. 2B.

Figure 3:
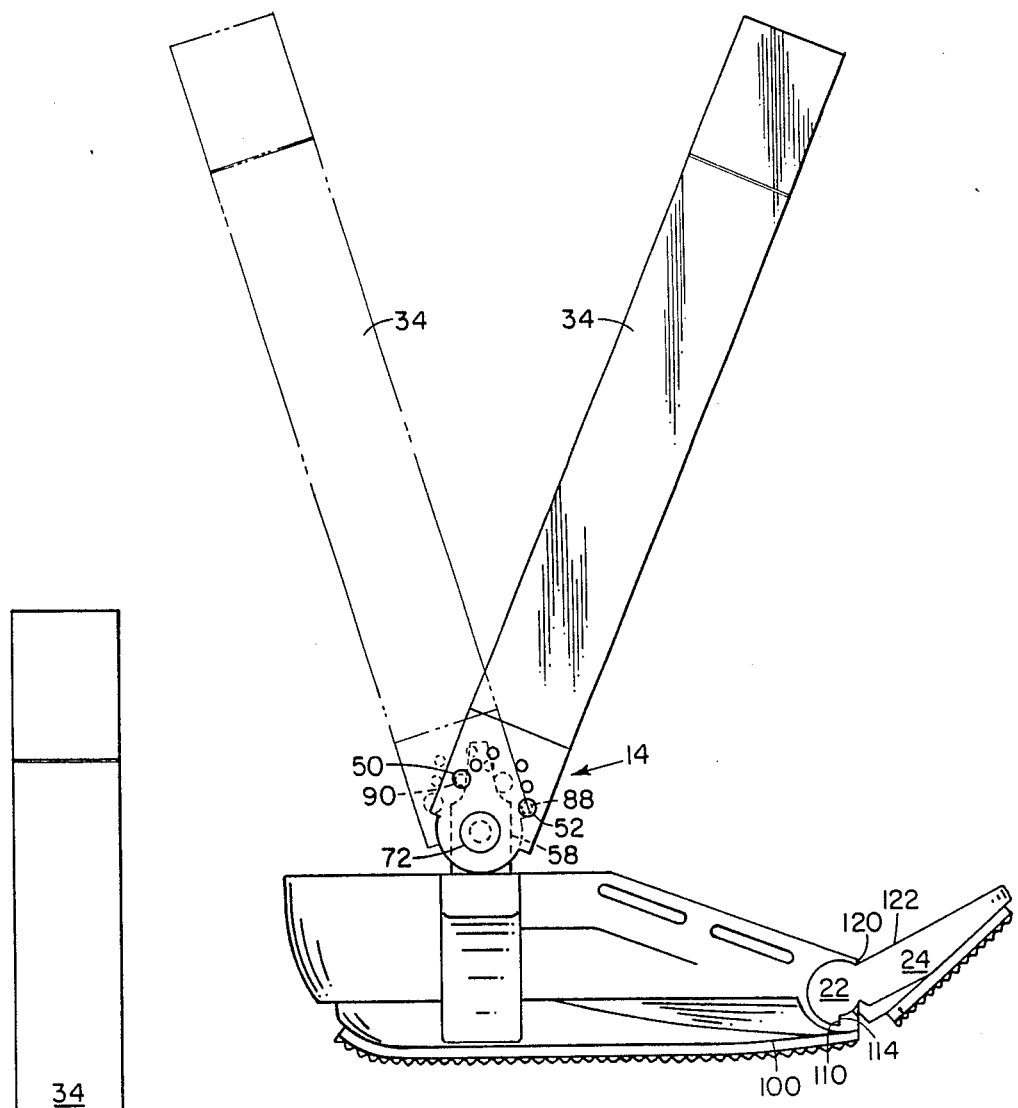
FIG. 3 is a side elevation view of the present invention in 20° plantarflexion with the toe hinge at 30° travel. Also shown in FIG. 3 in dotted lines is 20° dorsiflexion.

FIG. 3 illustrates brace 34 with pins 50 and 52 in adjustment holes 90 and 88 thereby providing 20° flexion in both the plantar and dorsal directions. Further flexion is limited as pins 50 and 52 abut against the arcuated edges of riser 58. FIG. 3 also illustrates the upward flexion of toe member 24 as it pivots about hinge 22. Because toe member 24 is able to flex, the overall thickness of sole member 100 may be kept to a minimum. As may be seen in FIGS. 1-3, sole member 100 in midfoot portion 20 has a generally flat, non-arcuated bottom surface to which is affixed the thin flat traction thread 46 for full, flat contact of the midfoot portion with the ground or walking surface during walking. This flat bottom surface of midfoot portion 20 extends from behind the toe hinge 22 to just forward of the heel base 18 (FIG. 1). This minimum height of the sole 100 eliminates the need for a thick arcuated sole used in prior art devices.

Figure 4:
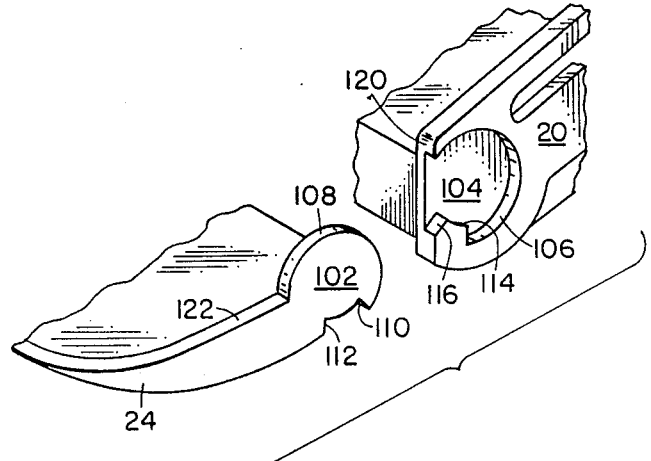
FIG. 4 is a partial exploded perspective view of the toe hinge of the present invention.

Details of hinge 22 are illustrated in FIG. 4. Toe member 24 has the male portion 102 of hinge 22 while the female portion 104 is formed in midfoot portion 20. When assembled, male portion 102 fits into the female portion 104. The outer surface 108 of male portion 102 rotates on and is supported by the inner surface 106 of female portion 104. The degree of flexion of toe member 24 in toe hinge 22 is limited by upward limiting shoulder 110 and downward limiting shoulder 112 on male portion 102 abutting against upward abutting shoulder 114 and downward abutting shoulder 116 on female portion 104. In FIG. 3, upward limiting shoulder 110 is shown abutting upward abutting shoulder 114. In FIG. 2, downward flexion is shown being limited such that the top edge 122 of toe member 24 is limited to being substantially in parallel alignment with the generally flat, non-arcuated bottom surface of midfoot portion 20 by abutment of downward limiting shoulder 112 with downward abutting shoulder 116. The degree of upward flexing is also limited by the abutment of midfoot abutting shoulder 120 against the top edge 122 of toe member 24.

In the preferred embodiment of the present invention, toe member 24, hinge 22, and midfoot portion 20 are made of molded plastics which require little or no maintenance. Hinge 22 has been designed as simply as possible to easily flex and then return to the downward position by its own weight. Graphite or other suitable lubricants may be applied to hinge 22 to provide for smooth flexing of toe member 24.

While the invention has been described in connection with a preferred embodiment, it is not intended to limit the invention to the particular form set forth, but, on the contrary, it is intended to cover alternatives, modifications, and equivalents, as may be included within the spirit and scope of the invention as defined by the appended claims.

I claim:

1. An orthopedic restraint apparatus comprising:

a foot support member, said foot support member having a heel base, a midfoot portion and a toe member pivotally connected thereto, said midfoot portion having a generally flat, non-arcuate bottom surface with a thin, flat traction tread affixed to said bottom surface so as to provide full, flat contact of said midfoot portion with the ground during walking, said bottom surface extending from immediately behind said toe member of said foot support to immediately forward of said heel base of said foot support, said foot support member further having rigidly attached thereto a first and a second vertical riser, said risers extending upwardly from opposite sides of said support member;

first and second lower leg brace members pivotally attached at first ends to said first and said second risers, respectively, each of said brace members further comprising ankle joints capable of adjusting the flexion of said brace members;

said toe member hingedly attached to a forward end of said foot support member and capable of flexion in the upward direction, said toe member further comprising male hinge portions on opposite sides of said toe member and said midfoot portion having female hinge portions positioned, for cooperative engagement with said male hinge portions, each of said male hinge portions further comprising upward and downward limiting shoulders, and each of said female hinge portions further comprising upward and downward abutting shoulders cooperating with said limiting shoulders to control the degree of downward flexion of said toe member such that the top edge of said toe member is limited to being substantially in parallel alignment with said generally flat, non-arcuated bottom surface of said midfoot portion of said foot support member.

* * * * *